(12) United States Patent
Jang et al.

(10) Patent No.: US 12,385,889 B2
(45) Date of Patent: Aug. 12, 2025

(54) DEVICE AND METHOD FOR ANOMALY DETECTION OF GAS SENSOR

(71) Applicant: ELECTRONICS AND TELECOMMUNICATIONS RESEARCH INSTITUTE, Daejeon (KR)

(72) Inventors: YongWon Jang, Daejeon (KR); Hwin Dol Park, Daejeon (KR); Chang-Geun Ahn, Sejong-si (KR); Do Hyeun Kim, Goyang-si (KR); Seunghwan Kim, Daejeon (KR); Hyung Wook Noh, Sejong-si (KR); Kwang Hyo Chung, Daejeon (KR); Jae Hun Choi, Sejong-si (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 697 days.

(21) Appl. No.: 17/513,567

(22) Filed: Oct. 28, 2021

(65) Prior Publication Data

US 2022/0187262 A1 Jun. 16, 2022

(30) Foreign Application Priority Data

Dec. 15, 2020 (KR) .................. 10-2020-0175155

(51) Int. Cl.
*G01N 33/00* (2006.01)
*G06N 3/045* (2023.01)

(52) U.S. Cl.
CPC ......... *G01N 33/0006* (2013.01); *G06N 3/045* (2023.01)

(58) Field of Classification Search
CPC .................................................. G01N 33/0006
(Continued)

(56) References Cited

U.S. PATENT DOCUMENTS 6,286,493 B1  9/2001  Aoki
8,356,002 B2  1/2013  Kim et al.
(Continued)

FOREIGN PATENT DOCUMENTS

EP  3215815 B1  5/2020
JP  10-300703 A  11/1998
(Continued)

OTHER PUBLICATIONS

Cho. Translation of KR20200085491A. Published Jul. 2020. Accessed Jan. 2024. (Year: 2020).*

(Continued)

*Primary Examiner* — Walter L Lindsay, Jr.
*Assistant Examiner* — Philip T Fadul
(74) *Attorney, Agent, or Firm* — LRK PATENT LAW FIRM (57) ABSTRACT

Disclosed are a device and a method for anomaly detection of a gas sensor. The device includes a measuring unit that extracts a characteristic of a gas supplied from the outside, generates data based on the extracted characteristic, and outputs the data, and a data processing unit that receives the data, determines whether an error occurs in the data, and outputs an anomaly detection result based on a result of determining whether the error occurs in the data. The measuring unit performs a calibration operation or an environment adjusting operation before extracting the characteristic, and the data processing unit determines whether the error occurs in the data, based on machine learning.

15 Claims, 7 Drawing Sheets

(58) Field of Classification Search
 USPC .......................................................... 73/1.06
 See application file for complete search history.

(56) References Cited

U.S. PATENT DOCUMENTS

| | | | |
|---|---|---|---|
| 10,101,298 B1 * | 10/2018 | Zhang | ................ G01N 33/0047 |
| 10,151,687 B2 | 12/2018 | Young et al. | |
| 2013/0327124 A1 | 12/2013 | Schneider et al. | |
| 2019/0297381 A1 | 9/2019 | Chung et al. | |
| 2020/0097850 A1 | 3/2020 | Bae et al. | |
| 2023/0010457 A1 * | 1/2023 | Hildebrand | ........ G01N 33/0067 |

FOREIGN PATENT DOCUMENTS

| | | | |
|---|---|---|---|
| JP | 3570274 B2 | 9/2004 | |
| JP | 2013539043 A | 10/2013 | |
| KR | 10-2015-0010138 A | 1/2015 | |
| KR | 10-2017-0139663 A | 12/2017 | |
| KR | 10-2018-0065589 A | 6/2018 | |
| KR | 10-1874085 B1 | 8/2018 | |
| KR | 10-1940501 B1 | 1/2019 | |
| KR | 10-2019-0047878 A | 5/2019 | |
| KR | 10-2031123 B1 | 11/2019 | |
| KR | 20200001516 U | 7/2020 | |
| KR | 20200085491 A | 7/2020 | |

OTHER PUBLICATIONS

GasDNA. Translation of KR20200001516U. Published Jul. 2020. Accessed Jan. 2024. (Year: 200).*

\* cited by examiner

DEVICE AND METHOD FOR ANOMALY DETECTION OF GAS SENSOR

CROSS-REFERENCE TO RELATED APPLICATION

This application claims priority under 35 U.S.C. § 119 to Korean Patent Application No. 10-2020-0175155 filed on Dec. 15, 2020, in the Korean Intellectual Property Office, the disclosure of which is incorporated by reference herein in its entirety.

BACKGROUND

1. Field of the Invention

The present disclosure relates to a device and a method for anomaly detection of a gas sensor, and more particularly, relates to a device and a method for automatically performing a preparation operation necessary to drive a gas sensor and automatically detecting the anomaly of the gas sensor.

2. Description of Related Art

Various kinds of sensors are used to measure a characteristic of a gas and have different characteristics. To accurately measure a characteristic of a gas, a sensor requires calibration appropriate for a characteristic thereof, and some sensors require a calibration operation such as a pre-operation. Also, the performance of the sensor may degrade over usage time, but unless the sensor operates in a complete failure state, it is difficult to determine whether a result of measuring a gas characteristic is erroneous. Accordingly, in general, an operator draws on his/her experience to perceive the anomaly of the gas characteristic measuring result and checks the anomaly of the sensor by again measuring a gas characteristic or replacing the sensor.

Various studies for automatically detecting an error of a gas sensor have been conducted, but unless there is an explicit problem such as the event that the gas sensor is completely broken or the event that a normal output is not derived under an ideal condition, it is difficult to determine whether an error occurs at the sensor in operation. For example, a method of detecting an error of a gas sensor through a statistical method requires an environment that is uniformly maintained in gas measurement, and a determination (or discrimination) error may occur when any other signal being not a measurement target is introduced into the sensor. As another example, in a method of detecting a measurement error based on a multi-step error analysis method, data errors or data pattern errors must be set in advance, but all kinds of data errors or data pattern errors cannot be set in advance.

SUMMARY

Embodiments of the present disclosure provide a device and a method automatically performing a preparation operation necessary to drive a gas sensor and automatically detecting the anomaly of the gas sensor.

According to an embodiment, an anomaly detecting device includes a measuring unit that extracts a characteristic of a gas supplied from the outside, generates data based on the extracted characteristic, and outputs the data, and a data processing unit that receives the data, determines whether an error occurs in the data, and outputs an anomaly detection result based on a result of determining whether the error occurs in the data. The measuring unit performs a calibration operation or an environment adjusting operation before extracting the characteristic, and the data processing unit determines whether the error occurs in the data, based on machine learning.

As an example, the measuring unit includes a power unit that supplies a circuit voltage and a heating voltage, a sensor unit that includes at least one gas sensor for measuring the gas supplied from the outside, a calibration unit that performs the calibration operation based on a driving condition of the sensor unit, an environment adjusting unit that performs the environment adjusting operation for adjusting a measurement environment of the sensor unit, and a control unit that controls the power unit, the sensor unit, the calibration unit, and the environment adjusting unit.

As an example, the at least one gas sensor measures a volatile organic compound (VOC)-based gas.

As an example, the calibration unit includes a storage vessel that stores a gas to be used in the calibration operation, a valve that adjusts an inflow of the gas to be used in the calibration operation, into the sensor unit, and a regulator that adjusts an inflow amount of the gas to be used in the calibration operation.

As an example, the data processing unit includes a data collecting unit that collects the received data, a data determining unit that determines whether the received data are abnormal, based on the machine learning, a data storage unit that stores the collected data and a result of determining whether the received data are abnormal, and a data learning unit that performs the machine learning based on the collected data and the determination result stored in the data storage unit.

As an example, the control unit stores information of the calibration operation performed by the calibration unit, aging information of the at least one gas sensor included in the sensor unit, and environment information obtained from the environment adjusting unit, and transfers the information of the calibration operation, the aging information of the at least one gas sensor, and the environment information to the data storage unit.

As an example, a reliability of the anomaly detection result output from the data processing unit is output based on the information of the calibration operation, the aging information of the at least one gas sensor, and the environment information transferred to the data storage unit.

As an example, the machine learning is based on a cycle-GAN (Generative Adversarial Network) network or a cascaded cycle-GAN network.

As an example, the anomaly detecting device further includes a display unit that displays the anomaly detection result or a notification unit that notifies the anomaly detection result.

As an example, the data processing unit derives the anomaly detection result at a regular time interval.

According to an embodiment, a method of detecting an anomaly of a gas sensor of an anomaly detecting device based on data measured from the gas sensor includes performing first machine learning based on normal data and abnormal data, sensing a measurement target gas, processing the data measured from the measurement target gas, and determining whether the data output from the gas sensor are abnormal. When it is determined that the data are abnormal, a signal indicating the anomaly of the gas sensor is output to the outside. When it is determined that the data are normal, second machine learning is performed based on a result of determining whether the data are abnormal.

As an example, the method further includes performing a calibration operation on the gas sensor, and performing an environment adjusting operation on the gas sensor.

As an example, the method further includes storing information of the calibration operation, aging information of the gas sensor, and information of the environment adjusting operation.

As an example, the method further includes outputting a reliability of the result of determining whether the data are abnormal, based on the information of the calibration operation, the aging information of the gas sensor, and the information of the environment adjusting operation.

As an example, the first machine learning and the second machine learning are based on a cycle-GAN (Generative Adversarial Network) network or a cascaded cycle-GAN network.

BRIEF DESCRIPTION OF THE DRAWINGS

The above and other objects and features of the present disclosure will become apparent by describing in detail embodiments thereof with reference to the accompanying drawings.

DETAILED DESCRIPTION

Below, embodiments of the present disclosure will be described in detail and clearly to such an extent that one skilled in the art easily carries out the present disclosure.

The terms used in the specification are provided to describe the embodiments, not to limit the present disclosure. As used in the specification, the singular terms "a," "an" and "the" are intended to include the plural forms as well, unless the context clearly indicates otherwise. The terms "comprises" and/or "comprising," when used in the specification, specify the presence of steps, operations, elements, and/or components, but do not preclude the presence or addition of one or more other steps, operations, elements, components, and/or groups thereof.

In the specification, the term "first and/or second" will be used to describe various elements but will be described only for the purpose of distinguishing one element from another element, not limiting an element of the corresponding term. For example, without departing the scope of the present disclosure, a first element may be referred to as a second element, and similarly, a second element may be referred to as a first element.

Unless otherwise defined, all terms (including technical and scientific terms) used in the specification should have the same meaning as commonly understood by those skilled in the art to which the present disclosure pertains. The terms, such as those defined in commonly used dictionaries, should not be interpreted in an idealized or overly formal sense unless expressly so defined herein. The same reference numerals represent the same elements throughout the specification.

Figure 1:
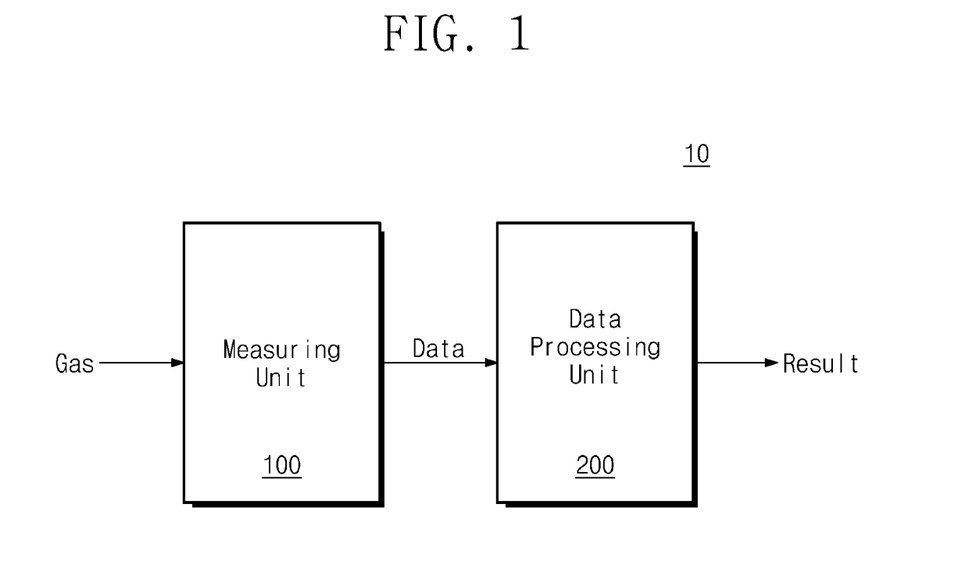
FIG. 1 is a block diagram illustrating an anomaly detecting device for gas sensor, according to an embodiment of the present disclosure.

FIG. 1 is a block diagram illustrating an anomaly detecting device 10 for gas sensor, according to an embodiment of the present disclosure. Referring to FIG. 1, according to an embodiment of the present disclosure, the anomaly detecting device 10 for gas sensor may include a measuring unit 100 and a data processing unit 200.

The measuring unit 100 may be supplied with a gas from the outside. The gas that is supplied to the measuring unit 100 may be an unspecified gas. In an embodiment, the unspecified gas may be a volatile organic compound (VOC)-based gas. The measuring unit 100 may perform analog-to-digital conversion on an obtained characteristic gas to generate data. The measuring unit 100 may output the generated data to the data processing unit 200. Operations, characteristics, and components of the measuring unit 100 will be described in more detail with reference to FIG. 2.

The data processing unit 200 may perform machine learning. The data processing unit 200 may determine (or discriminate) an anomaly of the measuring unit 100 from the data received from the measuring unit 100, based on a result of the machine learning. In more detail, the data processing unit 200 may determine whether a gas sensor included in the measuring unit 100 is abnormal. The data processing unit 200 may output a result of determining the anomaly of the gas sensor to the outside. Operations, characteristics, and components of the data processing unit 200 will be described in more detail with reference to FIG. 3.

Although not illustrated in FIG. 1, the anomaly detecting device 10 for gas sensor according to the present disclosure may further include a display unit for displaying the determination result to be output to the outside or an alarm unit for notifying the determination result. When the anomaly of the gas sensor is sensed by the anomaly detecting device 10, the display unit may visually provide a user with information about the anomaly of the gas sensor. When the anomaly of the gas sensor is sensed by the anomaly detecting device 10, the alarm unit may provide the user with an alarm notification associated with the occurrence of the anomaly of the gas sensor.

The anomaly detecting device 10 for gas sensor according to the present disclosure may automatically adjust complicated usage conditions of various sensors based on a status of the measuring unit 100 and may automatically perform calibration if necessary. Also, without needing to set all kinds of data errors or data pattern errors in advance, the anomaly detecting device 10 for gas sensor according to the present disclosure may sense the anomaly of the measuring unit 100 based on the machine learning of the data processing unit 200, thus improving the reliability of data output from the gas sensor.

Also, even in the case where one of normal data and abnormal data is insufficient, the anomaly detecting device 10 for gas sensor according to the present disclosure may perform learning for detecting an error of data measured from the gas sensor. Accordingly, even in the case where it is not easy to collect abnormal data, the anomaly detecting device 10 for gas sensor according to the present disclosure may perform learning sufficient to sense the anomaly of the gas sensor.

Figure 2:
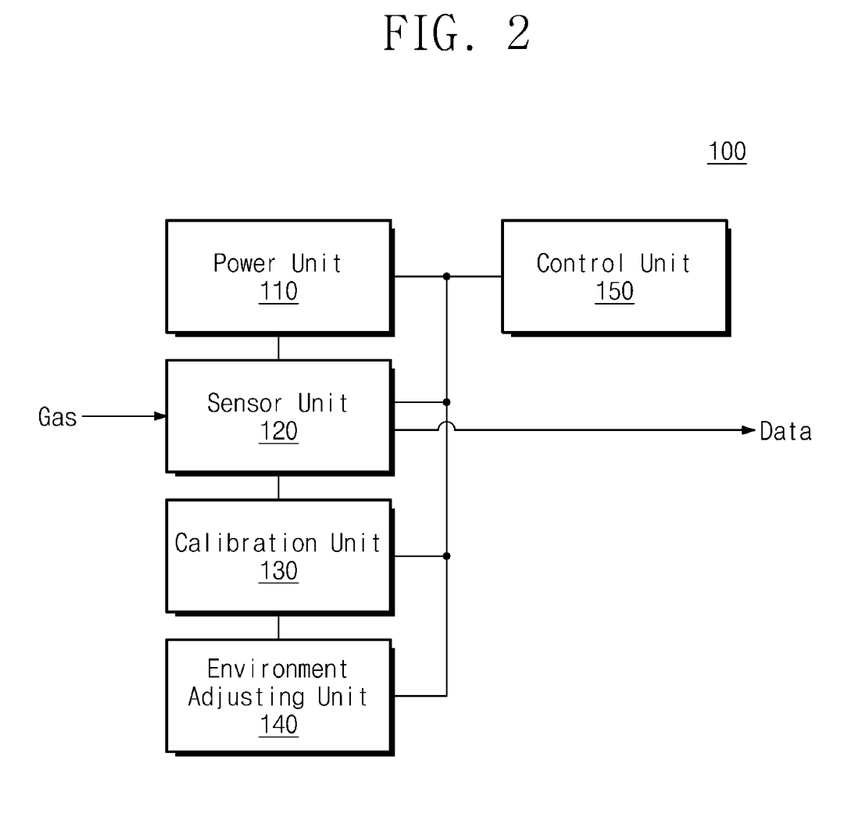
FIG. 2 is a block diagram illustrating a measuring unit in detail, according to an embodiment of the present disclosure.

FIG. 2 is a block diagram illustrating the measuring unit 100 in detail, according to an embodiment of the present disclosure. Referring to FIG. 2, the measuring unit 100 may include a power unit 110, a sensor unit 120, a calibration unit 130, an environment adjusting unit 140, and a control unit 150.

The power unit 110 may supply a voltage based on information about the power standard such as a circuit voltage of a gas sensor included in the sensor unit 120 and a heating voltage. An example of an aspect of the voltage supplied from the power unit 110 will be described in detail in FIG. 4.

The sensor unit 120 may include one or more gas sensors for sensing a gas. In the case where the sensor unit 120 includes a plurality of gas sensors, the gas sensors may be different sensors that sense different gases as target materials. In other words, the sensor unit 120 may include a gas sensor or combinations of the plurality of gas sensors. The sensor unit 120 may sense a characteristic of a gas introduced from the outside. For example, the characteristic of the gas thus sensed may include a gas concentration, a gas volume, etc. The sensor unit 120 may output gas characteristics sensed from various gas sensors through analog-to-digital conversion as data. One or more gas sensors included in the sensor unit 120 may be implemented to be removable.

The calibration unit 130 may check and adjust the accuracy of the sensor unit 120, based on a gas characteristic of a standard state and an external environment. In more detail, the calibration unit 130 may perform the calibration operation for adjusting the characteristic of the gas introduced into the sensor unit 120 so as to be matched with the gas characteristic of the standard state. Although not illustrated in FIG. 2, the calibration unit 130 may include a gas necessary for the calibration operation, a storage vessel for storing the gas, a valve adjusting an inflow of the gas, and a regulator adjusting an inflow amount of the gas.

The environment adjusting unit 140 may collect measurement environment information for the purpose of maintaining an ideal environment for measuring a gas characteristic. For example, the measurement environment information may include a temperature, a humidity, an oxygen concentration, etc. The environment adjusting unit 140 may adjust a measurement environment based on the collected measurement environment information such that the sensor unit 120 is capable of maintaining an ideal environment.

The control unit 150 may store data associated with operations and preparation conditions of the power unit 110 and the sensor unit 120. For example, the control unit 150 may store the power standard information of the sensor unit 120 and driving information of the sensor unit 120. Also, the control unit 150 may store information about calibration performed by the calibration unit 130, aging information of the gas sensor included in the sensor unit 120, and environment information obtained from the environment adjusting unit 140. Although not illustrated in FIG. 2, the information stored in the control unit 150 may be output to the data processing unit 200 (refer to FIG. 1).

Also, the control unit 150 may control operations of the power unit 110, the sensor unit 120, the calibration unit 130, and the environment adjusting unit 140. For example, the control unit 150 may control the power unit 110 based on the stored power standard information such that an appropriate power is supplied to the sensor unit 120; when calibration is required, the control unit 150 may allow the calibration unit 130 to supply the gas and to perform calibration. Also, based on the driving information of the sensor unit 120, the control unit 150 may control the environment adjusting unit 140 for the purpose of adjusting the measurement environment of the sensor unit 120; when preparation for measurement of a gas characteristic is completed by the power unit 110, the calibration unit 130, and the environment adjusting unit 140, the control unit 150 may allow a measurement sample to flow into the sensor unit 120 and may allow the sensor unit 120 to measure a gas characteristic.

Although not illustrated in FIG. 2, the measuring unit 100 according to an embodiment of the present disclosure may further include a pump for adjusting a gas inflow, a mass flow controller (MFC) for adjusting a gas inflow speed and a mass of a gas, or a gauge for checking a pressure of a gas. The above configuration of the measuring unit 100 is only an example for some embodiments of the present disclosure, not intended to limit the components of the measuring unit 100 according to an embodiment of the present disclosure.

Figure 3:
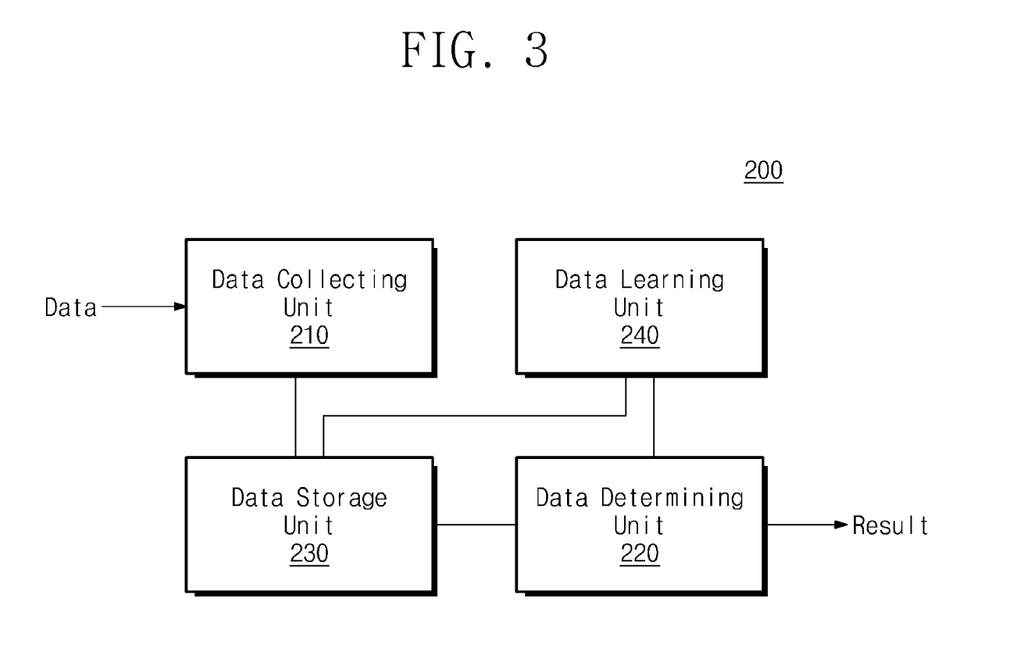
FIG. 3 is a block diagram illustrating a data processing unit in detail, according to an embodiment of the present disclosure.

FIG. 3 is a block diagram illustrating the data processing unit 200 in detail, according to an embodiment of the present disclosure. Referring to FIG. 3, the data processing unit 200 may include a data collecting unit 210, a data determining unit 220, a data storage unit 230, and a data learning unit 240.

The data collecting unit 210 may collect data output from the measuring unit 100 (refer to FIG. 1). Also, the data collecting unit 210 may collect additional information of the sensor unit 120 (refer to FIG. 2) output from the measuring unit 100. For example, the additional information may include calibration information, aging information of a gas sensor, and data-measured environment information, which are stored in the control unit 150 (refer to FIG. 2) of the measuring unit 100. The collected data may be transferred into and stored in the data storage unit 230.

The data determining unit 220 may receive the collected data from the data determining unit 220. The data determining unit 220 may determine the anomaly of the input data and the reliability of the gas sensor. A criterion that is used for the data determining unit 220 to determine the anomaly is a result of machine learning performed by the data determining unit 220. For example, the determination criterion of the data determining unit 220 may include a profile of a reaction start portion when a measurement target gas flows into the sensor unit 120, a reaction aspect (or pattern) when a contact time of the gas and a sensor of the sensor unit 120 continues, etc.

Meanwhile, in addition to information about whether data are abnormal, the reliability of the gas sensor derived from the data determining unit 220 may be provided to the outside as a determination result. For example, the determination result provided to the outside may indicate that data currently collected from the gas sensor has the reliability of 90%, that is, the data are normal or may indicate that data currently collected from the gas sensor has the reliability of 85%, that is, the data are abnormal. Because the gas sensor may operate normally and may then perform an abnormal operation, the collected data may be determined in units of given time interval, that is, in units of time window.

The data storage unit 230 may store data collected by the data collecting unit 210 and a result determined by the data determining unit 220. For example, data that are stored in the data storage unit 230 may be time-series data.

The data learning unit 240 may perform machine learning based on the data stored in the data storage unit 230. To make the accuracy of the data determining unit 220 high, the data learning unit 240 may perform continuous machine learning based on new data newly stored in the data storage unit 230.

The machine learning of the data processing unit 200 may be performed by the data determining unit 220 and the data learning unit 240, and may be based on a cycle-generative adversarial network (cycle-GAN) network or a cascaded cycle-GAN network. A machine learning principle according to an embodiment of the present disclosure will be described in detail with reference to FIG. 5.

Figure 4:
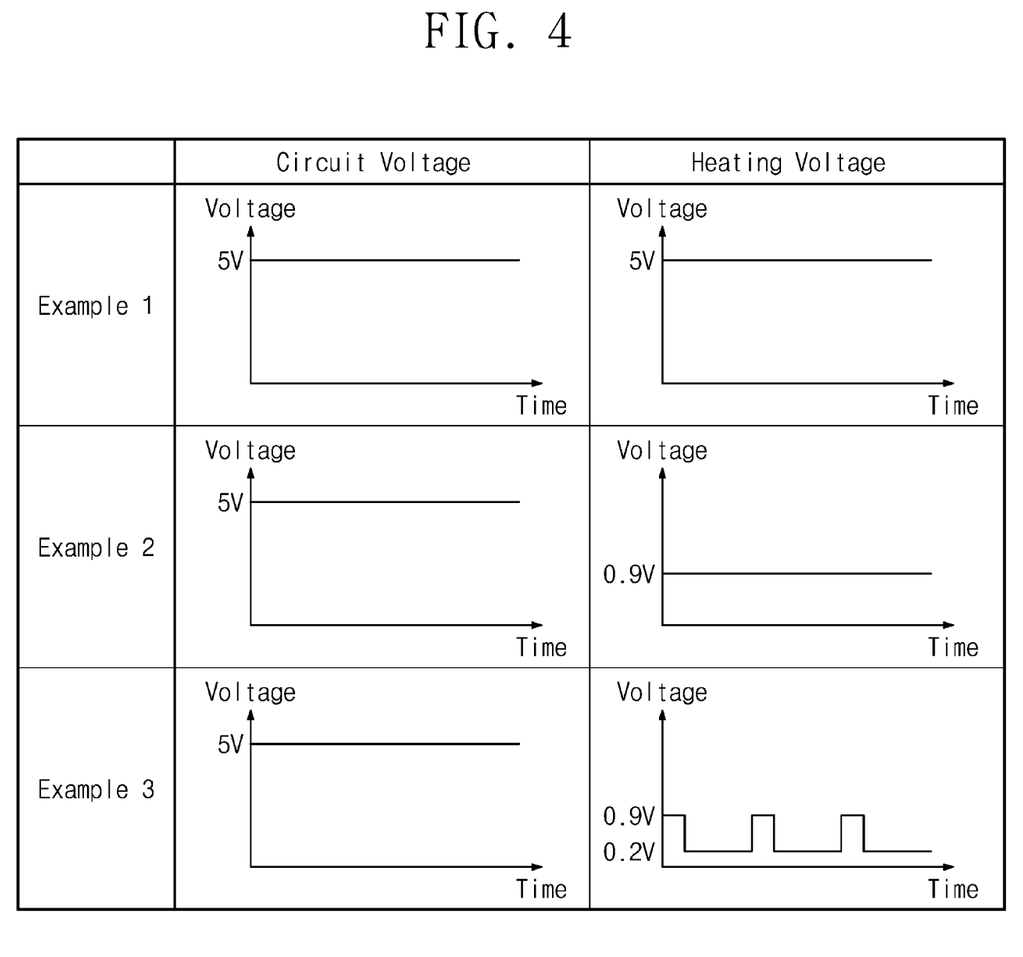
FIG. 4 is a diagram illustrating an aspect of a voltage supplied from a power unit, according to an embodiment of the present disclosure.

FIG. 4 is a diagram illustrating an aspect of a voltage supplied from the power unit 110 (refer to FIG. 2), according to an embodiment of the present disclosure. A value of a voltage that is supplied from the power unit 110 may be provided based on the power standard information of the gas sensor included in the sensor unit 120 (refer to FIG. 2). For example, the voltage value may be a value that is a constant value or varies periodically.

In an embodiment, in the case where the gas sensor included in the sensor unit 120 is implemented solely, the power unit 110 may supply a voltage to the gas sensor based on power standard information of the corresponding gas sensor. The case of example 1 corresponds to the case where a circuit voltage for driving a gas sensor is 5 V and a heating voltage for adjusting a temperature of the gas sensor is 5 V, and the case of example 2 means the case where the circuit voltage is 5 V and the heating voltage is 0.9 V. The case of example 3 means that the circuit voltage of the gas sensor that is 5 V is uniformly supplied and the heating voltage of the gas sensor is supplied in the form of a pulse voltage periodically varying within a range from 0.2 V to 0.9 V.

In an embodiment, in the case where the gas sensor includes a first gas sensor, a second gas sensor, and a third gas sensor, the power unit 110 may supply a voltage to each gas sensor based on power standard information of each gas sensor. In the case where the first gas sensor requires the circuit voltage of 5 V and the heating voltage of 5 V, the second gas sensor requires the circuit voltage of 5 V and the heating voltage of 0.9 V, and the third gas sensor requires the circuit voltage of 5 V and the heating voltage periodically varying within a range from 0.2 V to 0.9 V, the power unit 110 may supply the voltages corresponding to example 1 to the first gas sensor, may supply the voltages corresponding to example 2 to the second gas sensor, and may supply the voltages corresponding to example 3 to the third gas sensor.

Figure 5:
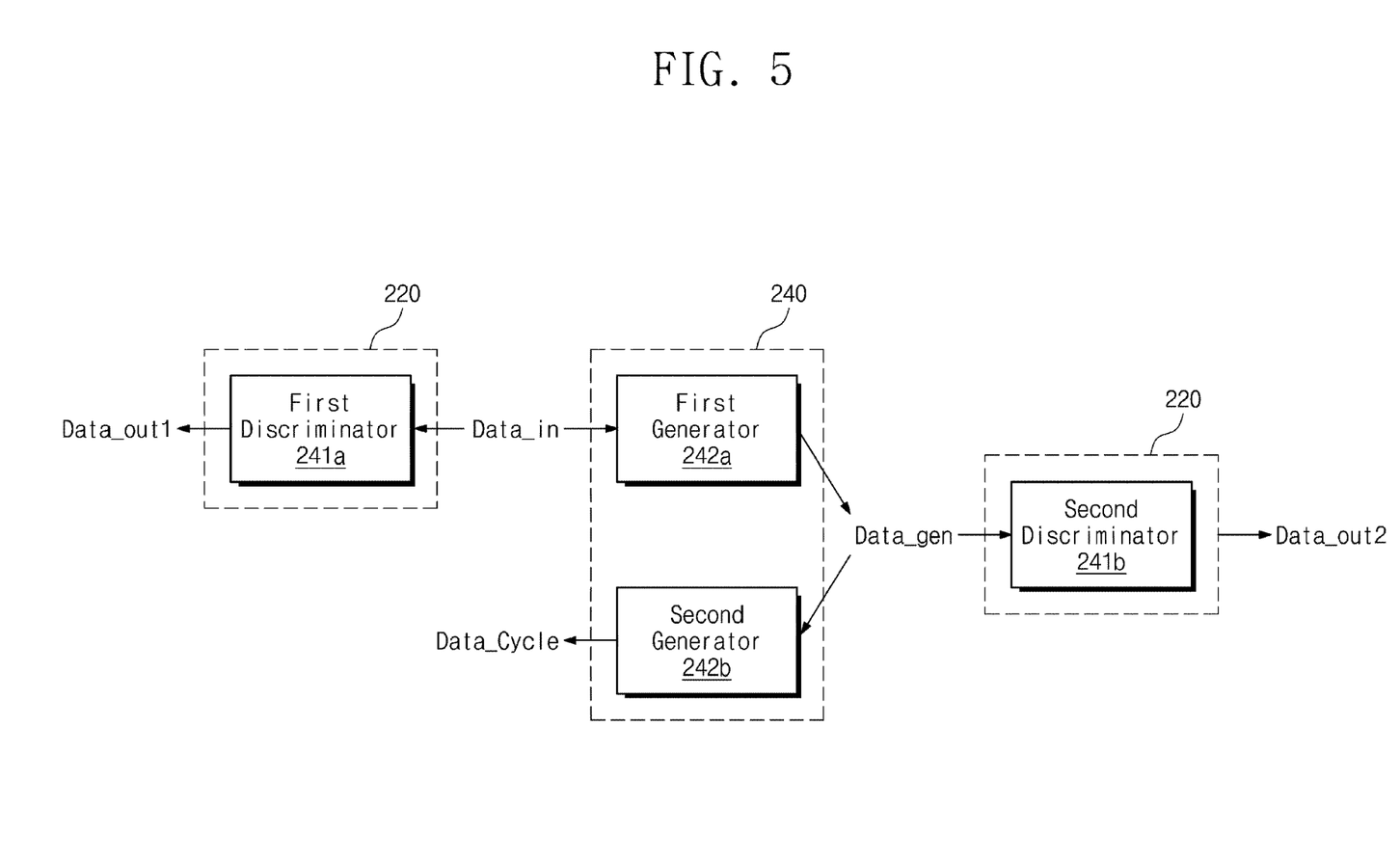
FIG. 5 is a diagram illustrating a machine learning principle, according to an embodiment of the present disclosure.

FIG. 5 is a diagram illustrating a machine learning principle according to an embodiment of the present disclosure. Machine learning according to an embodiment of the present disclosure may be based on the cycle-GAN network or the cascaded cycle-GAN network. The anomaly detecting device 10 (refer to FIG. 1) according to an embodiment of the present disclosure may overcome a limitation on automatic error detection due to the lack of abnormal data by performing machine learning based on the cycle-GAN network or the cascaded cycle-GAN network. For convenience of description, a first discriminator 241a and a second discriminator 241b disclosed in FIG. 5 are illustrated as independent blocks, but is implemented with substantially one component included in the data determining unit 220. Learning that is performed by the first discriminator 241a and the second discriminator 241b means machine learning that is performed by the data determining unit 220. Meanwhile, learning that is performed by a first generator 242a and a second generator 242b means machine learning that is performed by the data learning unit 240.

The first discriminator 241a and the second discriminator 241b may determine whether input data are failure data, normal data, or abnormal data. The failure data means data that are output when a failure obviously occurs at a gas sensor. Data that are obviously out of a data range in which data may be output from the gas sensor may be classified as failure data. The normal data means data that are normally measured and output by the gas sensor, and the abnormal data that are not failure data means data in which a measurement error occurs, not normal data. In the case where data are classified as failure data by the first discriminator 241a and the second discriminator 241b, there may be decided an output value indicating that failure data are derived without separate discrimination.

Meanwhile, normal data and abnormal data may be determined based on the machine learning that is performed by the first discriminator 241a, the second discriminator 241b, the first generator 242a, and the second generator 242b. The machine learning that is performed by the anomaly detecting device 10 according to the present disclosure may include initial learning and intermediate learning. The initial learning means machine learning, which enables the anomaly detecting device 10 to discriminate any data at a given level or higher, including the first learning, and the intermediate learning means machine learning, which is continuously performed by the anomaly detecting device 10, after the initial learning.

The initial learning may be performed based on a plurality of abnormal data and normal data. The plurality of abnormal data and normal data may be collected from the data collecting unit 210 (refer to FIG. 3). The normal data may satisfy all driving conditions of the sensor unit 120 (refer to FIG. 2) and may be generated through normal driving of the sensor unit 120. In contrast, in data measured through a gas sensor in a completed system, an appearance frequency of abnormal data is significantly lower than that of normal data. Accordingly, to secure sufficient abnormal data for the initial learning, the anomaly detecting device 10 according to the present disclosure may apply some conditions to derive abnormal data.

In an embodiment, the case where a gas sensor generates abnormal data includes the case where calibration for the gas sensor is not made; the case where the performance of the gas sensor decreases due to aging; the case where an operating condition of the gas sensor is not satisfied, such as the case where an operating voltage or heating voltage condition of a semiconductor-type gas sensor is not satisfied or the case where measurement is made in a place where oxygen is insufficient; the case where the gas sensor is not used for a long time; the case where a physical quantity of a measurement target, such as concentration or intensity, does not belong to a measurement range of the gas sensor; the case where an electrical connection of the gas sensor is not normal due to a poor contact; and the case where an output of normal data is impossible because the stability and normal operation of the gas sensor are disturbed. The anomaly detecting device 10 may perform the initial learning, based on abnormal data generated by artificially applying conditions of various examples and normal data generated through a normal operation of a gas sensor.

The collected normal data and abnormal data may be input data Data_in for the first discriminator 241a and the first generator 242a. In the case where abnormal data are input as the input data Data_in, the first discriminator 241a may determine whether the input data Data_in are normal. In the case where the first discriminator 241a determines abnormal data as abnormal, it may be regarded as the learning of the first discriminator 241a is properly performed. The first discriminator 241a may learn a determination criterion based on various normal data and abnormal data collected. The input data Data_in may be simultaneously transferred to the first discriminator 241a and the first generator 242a such that fake data similar to real data may be generated. To generate fake data similar to real data, the anomaly detecting device 10 according to the present disclosure may verify the fake data based on the cycle-GAN network or the cascaded cycle-GAN network and may perform machine learning based on a verification result.

Generated data Data_gen may be input to the second discriminator 241b. The second discriminator 241b may determine whether the input generated data Data_gen are normal. The second discriminator 241b may output the reliability of data, based on a value output from a decision function or a separate reliability applying process. The generated data Data_gen may be simultaneously transferred to the second discriminator 241b and the second generator 242b such that real data may be generated. Because the real data generated from the second generator 242b are data generated based on a cycle structure, the real data may be referred to as cycle data Data_cycle.

The anomaly detecting device 10 may compare the generated cycle data Data_cycle with the input data Data_in to check whether the learning of the anomaly detecting device 10 is properly performed (or whether to apply fake data to learning). For example, when the input data Data_in are abnormal data and the generated cycle data Data_cycle are abnormal data, it may be determined that the learning of the anomaly detecting device 10 is properly made, or it may be determined that fake data will be applied to learning. The initial learning may be sufficiently repeated and performed to such an extent as whether the input data Data_in are normal may be determined based on the collected abnormal data and normal data.

A machine learning principle of the intermediate learning is identical to that of the initial learning. However, the intermediate learning may be different from the initial learning in that machine learning is performed based on result data determined from the anomaly detecting device 10. In other words, the intermediate learning may perform machine learning by using result data derived through a preceding operation, instead of training data in the initial learning.

In the above description, the learning of the first discriminator 241a, the second discriminator 241b, the first generator 242a, and the second generator 242b in the initial learning may be performed simultaneously or sequentially. Also, the learning of the first discriminator 241a, the second discriminator 241b, the first generator 242a, and the second generator 242b in the intermediate learning may be performed simultaneously or sequentially.

Figure 6:
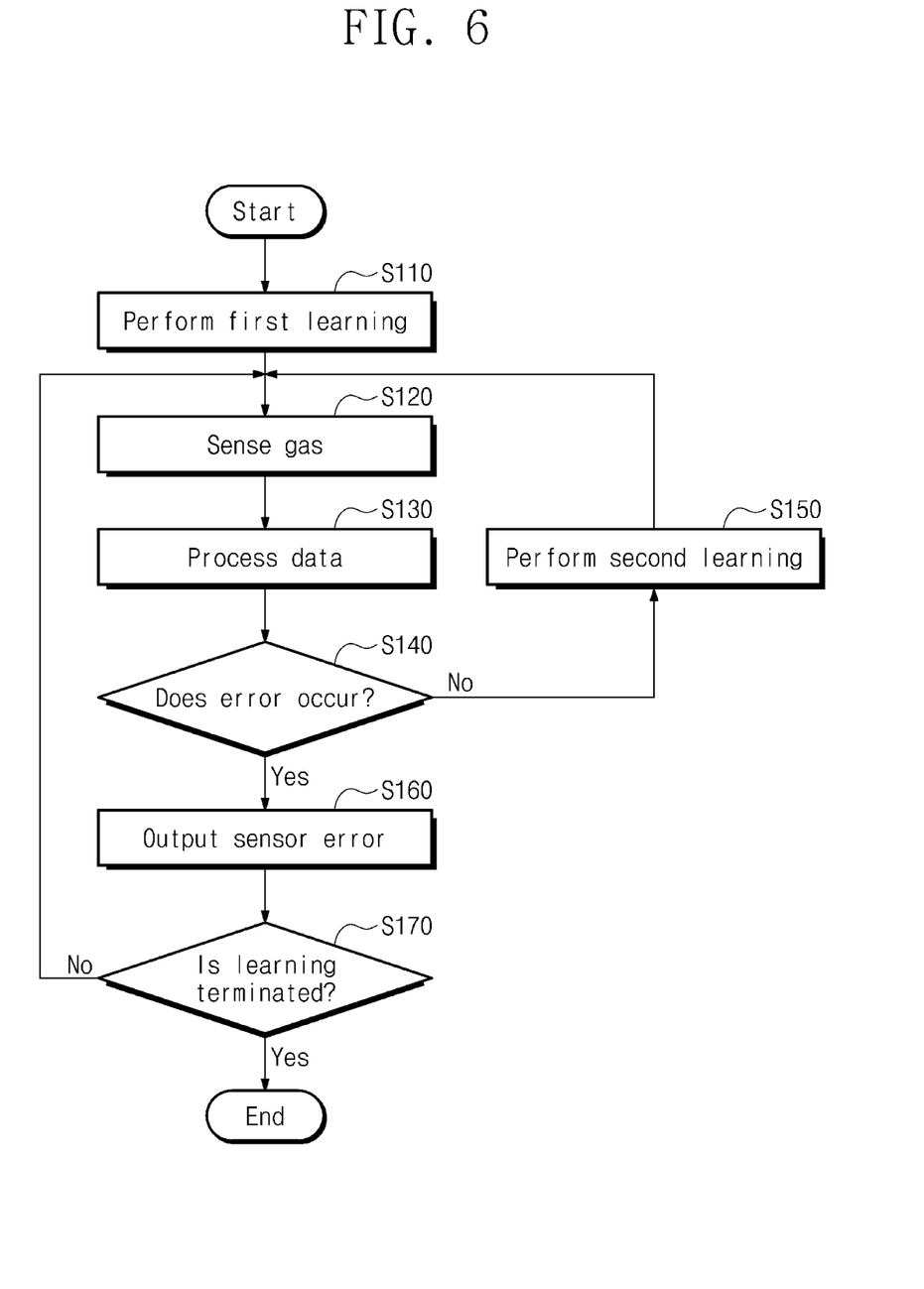
FIG. 6 is a flowchart for describing a method of sensing an anomaly of a gas sensor, according to an embodiment of the present disclosure.

FIG. 6 is a flowchart for describing a method of sensing an anomaly of a gas sensor, according to an embodiment of the present disclosure. Below, additional description duplicated with the components, functions, characteristics, and operations described with reference to FIGS. 1 to 5 will be omitted to avoid redundancy.

In operation S110, the anomaly detecting device 10 (refer to FIG. 1) may perform first learning. The first learning may mean the initial learning described with reference to FIG. 5, and the anomaly detecting device 10 may iteratively perform the first learning to sense the anomaly of gas measurement. When the first learning is sufficiently performed, the anomaly detecting device 10 may be in a preparation state for anomaly determination in measuring a gas supplied from the outside.

In operation S120, a gas sensor included in the anomaly detecting device 10 may sense the gas supplied from the outside. The measuring unit 100 (refer to FIG. 1) may extract a characteristic of the gas sensed by the sensor and may convert the extracted gas characteristic into data. The measuring unit 100 may provide the data to the data processing unit 200 (refer to FIG. 1). Before the gas sensing operation is performed, if necessary, a calibration operation and an environment adjusting operation may be performed in the anomaly detecting device 10.

In operation S130, the data processing unit 200 may process the input data. In more detail, the data processing unit 200 may collect the input data and may store the collected data in the data storage unit 230 (refer to FIG. 3) included in the data processing unit 200.

In operation S140, the data processing unit 200 may determine whether an anomaly occurs in the input data, based on the machine learning. When it is determined that the anomaly does not occur in the input data, the procedure proceeds to operation S150. In operation S150, the anomaly detecting device 10 may perform second learning based on a determination result, and the procedure may return to operation S120. The second learning may mean the intermediate learning described with reference to FIG. 5, and the anomaly detecting device 10 may iteratively perform the second learning to sense the anomaly of gas measurement. When it is determined that the anomaly occurs in the input data, the procedure proceeds to operation S160. In operation S160, the anomaly detecting device 10 may output, to the outside, a result value indicating that the anomaly of the gas sensor is detected.

In operation S170, the anomaly detecting device 10 may determine whether the learning of the data processing unit 200 is terminated. When it is determined that the learning of the data processing unit 200 is not terminated, the procedure may return to operation S120. When it is determined that the learning of the data processing unit 200 is terminated, the procedure may be terminated.

Figure 7:
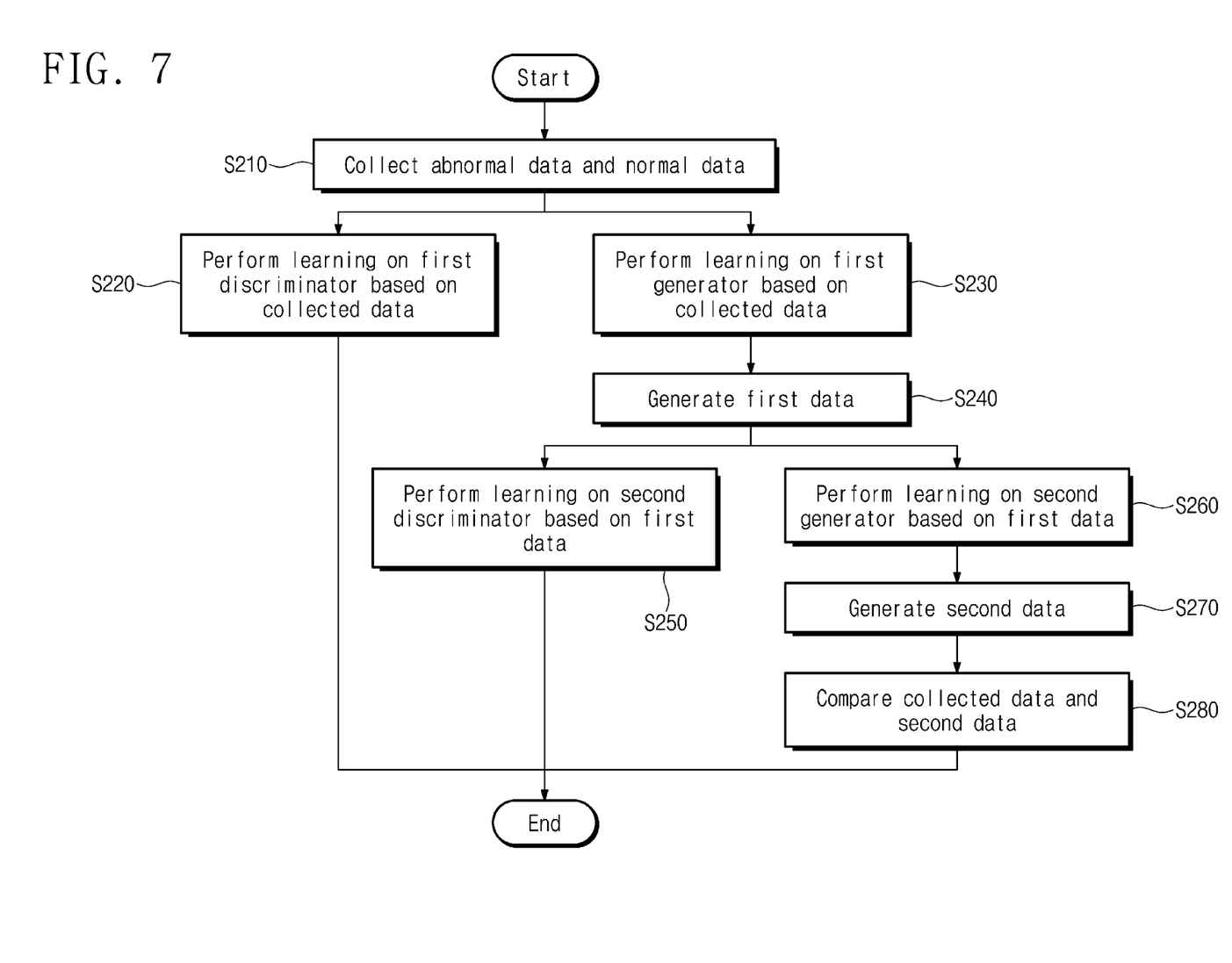
FIG. 7 is a flowchart for describing first learning in detail, according to an embodiment of the present disclosure.

FIG. 7 is a flowchart for describing first learning in detail, according to an embodiment of the present disclosure.

As described above, in operation S210, the anomaly detecting device 10 (refer to FIG. 1) may collect abnormal data and normal data from a gas sensor. The normal data may be derived when a normal operation is performed in a state where all driving conditions of the gas sensor are satisfied, and the abnormal data may be derived by artificially applying a condition in which a measurement error may occur at the gas sensor.

In operation S220, the anomaly detecting device 10 may perform machine learning on the first discriminator 241a (refer to FIG. 5), based on the collected abnormal data and normal data. The first discriminator 241a may perform machine learning for determining whether input data are normal.

In operation S230, the anomaly detecting device 10 may perform machine learning on the first generator 242a (refer to FIG. 5), based on the collected abnormal data and normal data. Operation S220 and operation S230 may be performed in parallel at the same time. In operation S230, the first generator 242a may perform machine learning for generating fake data associated with the input data. When the machine learning of the first generator 242a is sufficiently performed, the procedure may proceed to operation S240, in which the first generator 242a may use the input data and may generate first data being fake data based on the machine learning.

In operation S250, the second discriminator 241b (refer to FIG. 5) may receive the first data generated in operation S240 and may perform machine learning on the first data. The second discriminator 241b may perform machine learning for determining whether input data are normal.

In operation S260, the second generator 242b (refer to FIG. 5) may receive the first data generated in operation S240 and may perform machine learning on the first data. Operation S250 and operation S260 may be performed in parallel at the same time. When the machine learning of the second generator 242b is sufficiently performed, the procedure may proceed to operation S270, in which the second generator 242b may use the received first data and may generate second data being real data based on the machine learning.

In operation S280, the anomaly detecting device 10 may compare determination results for the input data and the second data. When the determination results for the input data and the second data are identical, it may be checked that the learning of the anomaly detecting device 10 is properly performed (or that fake data are capable of being used in learning). When the determination results for the input data and the second data are different, it may be checked that the learning of the anomaly detecting device 10 is not properly performed (or that fake data are incapable of being used in learning). When it is completely checked whether the machine learning is properly performed, the procedure may be terminated. When it is determined that the learning is not properly performed, the first discriminator 241a, the second discriminator 241b, the first generator 242a, or the second generator 242b may return to a state before the learning by using a specific small value as a weight or removing a weight.

Figure 8:
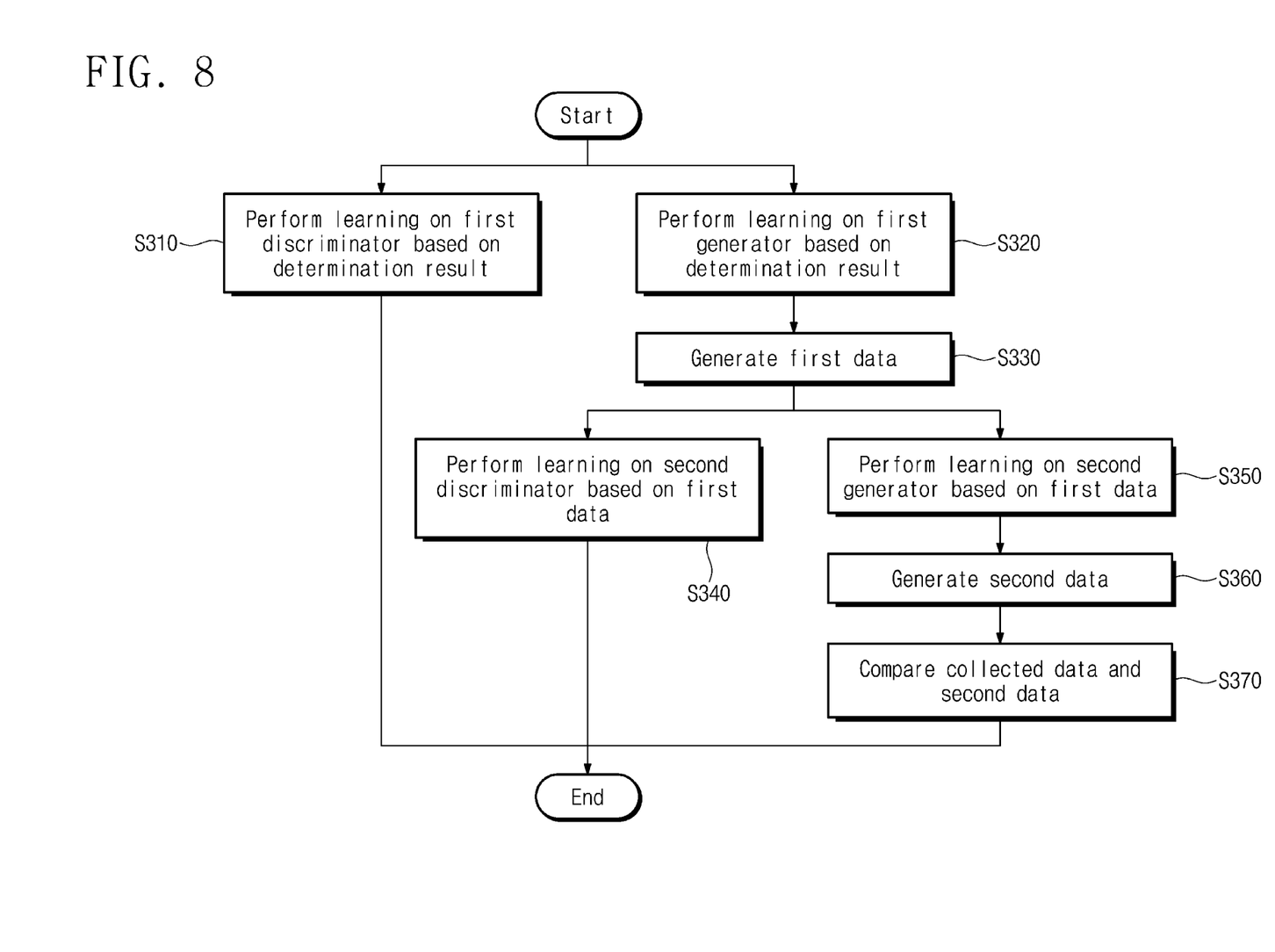
FIG. 8 is a diagram for describing second learning in detail, according to an embodiment of the present disclosure.

FIG. 8 is a diagram for describing second learning in detail, according to an embodiment of the present disclosure. In operation S150 disclosed in FIG. 6, when it is determined that the anomaly does not occur at the gas sensor, the anomaly detecting device 10 (refer to FIG. 1) may perform second learning based on a result of determining whether a gas sensor is abnormal.

In operation S310, the anomaly detecting device 10 may perform machine learning on the first discriminator 241a (refer to FIG. 5), based on a result of determination that is previously performed to check whether the gas sensor is abnormal. The first discriminator 241a may perform machine learning for determining whether input data are normal.

In operation S320, the anomaly detecting device 10 may perform machine learning on the first generator 242a (refer to FIG. 5), based on collected determination results. Operation S310 and operation S320 may be performed in parallel at the same time. In operation S320, the first generator 242a may perform machine learning for generating fake data associated with the input data. When the machine learning of the first generator 242a is sufficiently performed, the procedure may proceed to operation S330, in which the first generator 242a may use determination result data and may generate first data being fake data based on the machine learning.

In operation S340, the second discriminator 241b (refer to FIG. 5) may receive the first data generated in operation S330 and may perform machine learning on the first data. The second discriminator 241b may perform machine learning for determining whether input data are normal.

In operation S350, the second generator 242b (refer to FIG. 5) may receive the first data generated in operation S330 and may perform machine learning based on the first data. Operation S340 and operation S350 may be performed in parallel at the same time. When the machine learning of the second generator 242b is sufficiently performed, the procedure may proceed to operation S360, in which the second generator 242b may use the first data thus received and may generate second data being real data based on the machine learning.

In operation S370, the anomaly detecting device 10 may compare determination results for the input data and the second data. When the determination results for the input data and the second data are identical, it may be checked that the learning of the anomaly detecting device 10 is properly performed (or that fake data is capable of being used in learning). When the determination results for the input data and the second data are different, it may be checked that the learning of the anomaly detecting device 10 is not properly performed (or that fake data is incapable of being used in learning). When it is determined that the learning is not properly performed, the first discriminator 241a, the second discriminator 241b, the first generator 242a, or the second generator 242b may return to a state before the learning by using a specific small value as a weight or removing a weight. When it is completely checked whether the machine learning is properly performed, the procedure may be terminated.

A device and a method for anomaly detection of a gas sensor according to the present disclosure may automatically adjust complicated usage conditions of various sensors and may automatically perform calibration if necessary.

The device and the method for anomaly detection of a gas sensor according to the present disclosure may improve the reliability of data output from the gas sensor by sensing even the data output not only when the gas sensor fails but also when the gas sensor operates abnormally.

While the present disclosure has been described with reference to embodiments thereof, it will be apparent to those of ordinary skill in the art that various changes and modifications may be made thereto without departing from the spirit and scope of the present disclosure as set forth in the following claims.

What is claimed is:
1. An anomaly detecting device comprising:
a measuring unit configured to extract a characteristic of a gas supplied from the outside, to generate data based on the extracted characteristic, and to output the data; and
a data processing unit configured to receive the data, to determine whether an error occurs in the data, and to output an anomaly detection result based on a result of determining whether the error occurs in the data,
wherein the measuring unit performs a calibration operation or an environment adjusting operation before extracting the characteristic, and
wherein the data processing unit determines whether the error occurs in the data, based on machine learning,
wherein the measuring unit includes:
a power unit configured to supply a circuit voltage and a heating voltage;
a sensor unit including at least one gas sensor for measuring the gas supplied from the outside;
a calibration unit configured to perform the calibration operation based on a driving condition of the sensor unit;
an environment adjusting unit configured to perform the environment adjusting operation for adjusting a measurement environment of the sensor unit; and a control unit configured to control the power unit, the sensor unit, the calibration unit, and the environment adjusting unit, wherein the control unit is configured to store information of the calibration operation performed by the calibration unit, aging information of the at least one gas sensor included in the sensor unit, and environment information obtained from the environment adjusting unit, wherein the data processing unit includes:

a data collecting unit configured to collect the received data;

a data determining unit configured to determine whether the received data are abnormal, based on machine learning, wherein initial machine learning is based on abnormal data generated by artificially applying conditions of various abnormal data and normal data to the data determining unit, wherein the artificially generated abnormal data is verified based on a cycle-GAN (Generative Adversarial Network) network;

a data storage unit configured to store the collected data and a result of determining whether the received data are abnormal; and a data learning unit configured to perform the machine learning based on the collected data and the determination result stored in the data storage unit.

2. The anomaly detecting device of claim 1, wherein the at least one gas sensor measures a volatile organic compound (VOC)-based gas.

3. The anomaly detecting device of claim 1, wherein the calibration unit includes:

a storage vessel configured to store a gas to be used in the calibration operation;

a valve configured to adjust an inflow of the gas to be used in the calibration operation, into the sensor unit; and a regulator configured to adjust an inflow amount of the gas to be used in the calibration operation.

4. The anomaly detecting device of claim 1, wherein the control unit is configured to:

transfer the information of the calibration operation, the aging information of the at least one gas sensor, and the environment information to the data storage unit.

5. The anomaly detecting device of claim 4, wherein a reliability of the anomaly detection result output from the data processing unit is output based on the information of the calibration operation, the aging information of the at least one gas sensor, and the environment information transferred to the data storage unit.

6. The anomaly detecting device of claim 1, further comprising:

a display unit configured to display the anomaly detection result or a notification unit notifying the anomaly detection result.

7. The anomaly detecting device of claim 1, wherein the data processing unit derives the anomaly detection result at a regular time interval.

8. The anomaly detecting device of claim 1, wherein normal data is derived when a normal operation is performed in a state where all driving conditions of the gas sensor are satisfied and the abnormal data is derived by artificially applying a condition in which a measurement error may occur at the gas sensor.

9. The anomaly detecting device of claim 1, wherein the data determining unit comprises a first discriminator and a second discriminator which determine whether the input data is failure data, normal data or abnormal data.

10. The anomaly detecting device of claim 1, wherein the data learning unit comprises a first generator and a second generator to perform the machine learning based on the collected data and the determination result stored in the data storage unit.

11. The anomaly detecting device of claim 1, wherein the cycle-GAN network is a cascaded cycle-GAN network.

12. A method of detecting an anomaly of a gas sensor of an anomaly detecting device based on data measured from the gas sensor, the method comprising:

performing first machine learning based on normal data and abnormal data, wherein initial machine learning is based on abnormal data generated by artificially applying conditions of various abnormal data and normal data, wherein the artificially generated abnormal data is verified based on a cycle-GAN (Generative Adversarial Network) network;

performing a calibration operation on the gas sensor;

performing an environment adjusting operation on the gas sensor;

sensing a measurement target gas;

processing the data measured from the measurement target gas;

storing information of the calibration operation, aging information of the gas sensor, and information of the environment adjusting operation; and determining whether the data output from the gas sensor are abnormal, wherein, when it is determined that the data are abnormal, a signal indicating the anomaly of the gas sensor is output to the outside, and wherein, when it is determined that the data are normal, second machine learning is performed based on a result of determining whether the data are abnormal.

13. The method of claim 12, further comprising:

outputting a reliability of the result of determining whether the data are abnormal, based on the information of the calibration operation, the aging information of the gas sensor, and the information of the environment adjusting operation.

14. The method of claim 12, wherein normal data is derived when a normal operation is performed in a state where all driving conditions of the gas sensor are satisfied and the abnormal data is derived by artificially applying a condition in which a measurement error may occur at the gas sensor.

15. The method of claim 12, wherein the cycle-GAN network is a cascaded cycle-GAN network.

* * * * *